US011110146B2

(12) United States Patent
Hendrix et al.

(10) Patent No.: US 11,110,146 B2
(45) Date of Patent: Sep. 7, 2021

(54) METHODS FOR REDUCING PLATELET AGGREGATION AND TREATING CARDIOVASCULAR DISEASE AND OTHER MEDICAL DISORDERS

(71) Applicant: Paradise Health, Inc., Westlake Village, CA (US)

(72) Inventors: Curt Hendrix, West Lake Village, CA (US); Jack Joseph Kleid, West Lake Village, CA (US)

(73) Assignee: Paradise Health, Inc., Westlake Village, CA (US)

( * ) Notice: Subject to any disclaimer, the term of this patent is extended or adjusted under 35 U.S.C. 154(b) by 390 days.

(21) Appl. No.: 15/536,904

(22) PCT Filed: Dec. 18, 2015

(86) PCT No.: PCT/US2015/066641
§ 371 (c)(1),
(2) Date: Jun. 16, 2017

(87) PCT Pub. No.: WO2016/100801
PCT Pub. Date: Jun. 23, 2016

(65) Prior Publication Data
US 2019/0091277 A1 Mar. 28, 2019

Related U.S. Application Data

(60) Provisional application No. 62/094,488, filed on Dec. 19, 2014.

(51) Int. Cl.
*A61K 36/906* (2006.01)
*A61P 9/10* (2006.01)
*A61P 9/02* (2006.01)
*A61P 9/12* (2006.01)
*A61P 9/04* (2006.01)
*A61P 9/14* (2006.01)
*A61K 9/00* (2006.01)

(52) U.S. Cl.
CPC .......... *A61K 36/906* (2013.01); *A61K 9/0053* (2013.01); *A61P 9/02* (2018.01); *A61P 9/04* (2018.01); *A61P 9/10* (2018.01); *A61P 9/12* (2018.01); *A61P 9/14* (2018.01)

(58) Field of Classification Search
CPC ... A61K 36/906; A61K 36/9068; A61K 36/67
USPC ........................................ 424/734, 760, 776
See application file for complete search history.

(56) References Cited

U.S. PATENT DOCUMENTS

| 2005/0058728 A1 | 3/2005 | Randolph et al. |
| 2005/0260290 A1 | 11/2005 | Raskin et al. |
| 2006/0029686 A1 | 2/2006 | Randolph et al. |
| 2007/0031518 A1 | 2/2007 | Randolph et al. |
| 2008/0124412 A1* | 5/2008 | Raskin .................. A61K 31/12 424/756 |
| 2012/0322888 A1 | 12/2012 | Sugita et al. |

FOREIGN PATENT DOCUMENTS

| CN | 1096204 A | 12/1994 |
| CN | 1882354 A | 12/2006 |
| CN | 101181583 A | 5/2008 |
| CN | 101732307 A * | 6/2010 |
| JP | 2014-019648 A | 2/2014 |
| WO | WO-2005/025586 A1 | 3/2005 |
| WO | WO-2005/074959 A1 | 8/2005 |
| WO | WO-2006025307 A1 | 3/2006 |
| WO | WO-2008/064302 A2 | 5/2008 |

OTHER PUBLICATIONS

International Search Report and Written Opinion for PCT/US2015/066641 dated Mar. 17, 2016 (14 pages).
Falk, E. et al. "Update on acute coronary syndromes: the pathologists' view," *European Heart Journal* (2013) vol. 34, pp. 719-728.
Grzanna, R. et al. "Ginger—An Herbal Medicinal Product with Broad Anti-Inflammatory Actions," *J. Medicinal Food* (2005) vol. 8, No. 2, pp. 125-132.
Ilic, N. M. et al. "Anti-inflammatory Activity of Grains of Paradise (*Aframomum melegueta* Schum) Extract," *J. Agricultural Food Chem.* (2014) vol. 62, pp. 10452-10457.
Iwami, M. et al. "Extract of grains of paradise and its active principle 6-paradol trigger thermogenesis of brown adipose tissue in rats," *Autonomic Neurosci.* (2011) vol. 161, pp. 63-67.
Koo, K. L. K. et al. "Gingerols and Related Analogues Inhibit Arachidonic Acid-Induced Human Platelet Serotonin Release and Aggregation," *Thrombosis Research* (2001) vol. 103, pp. 387-397.
Paradoxine (TM) Publication obtained on Nov. 6, 2014. (4 pages).
Shih, H.-C. et al. "Synthesis of Analogues of Gingerol and Shogaol, the Active Pungent Principles from the Rhizomes of *Zingiber officinale* and Evaluation of Their Anti-Platelet Aggregation Effects," *Intl. J. Molecular Sci.* (2014) vol. 15, pp. 3926-3951.
Sugita, J. et al. "Grains of paradise (*Aframomum melegueta*) extract activates brown adipose tissue and increases whole-body energy expenditure in men," *Brit. J. Nutrition* (2013) vol. 110, No. 4, pp. 733-738.
Sugita, J. et al. "Daily Ingestion of Grains of Paradise (*Aframomum melegueta*) Extract Increases Whole-Body Energy Expenditure and Decreases Visceral Fat in Humans," *J. Nutritional Sci. Vitaminology* (2014) vol. 60, No. 1, pp. 22-27.
Umukoro, S. and Ashorobi, R.B. "Further studies on the antinociceptive action of aqueous seed extract of *Aframomum melegueta*," *J. Ethnopharmacology* (2007) vol. 109, No. 3, pp. 501-504. (abstract only).

(Continued)

Primary Examiner — Michael Barker
(74) Attorney, Agent, or Firm — Dechert LLP

(57) ABSTRACT

The invention provides therapeutic compositions containing ground seed of *Aframomum meleguata* or an extract thereof, and methods for using such compositions to reduce platelet aggregation and treat medical disorders in a patient, such as cardiovascular disease.

22 Claims, No Drawings

(56) References Cited

OTHER PUBLICATIONS

Akpanabiatu, M.I. et al. "Acute toxicity, biochemical and haematological study of Aframomum melegueta seed oil in male Wistar albino rats," Journal of Ethnopharmacology, vol. 150, (2013), pp. 590-594.

Database WPI, operated by Thomson Scientific, London, GB; Week 200872; AN 2008-M15427; CN 101181583A (Zhang M) May 21, 2008.

Database WPI, operated by Thomson Scientific, London, GB; Week 199624; AN 1996-231218; CN 1096204A (Li Y) Dec. 14, 1994.

Gbolade, A. "Ethnobotanical study of plants used in treating hypertension in Edo State of Nigeria," Journal of Ethnopharmacology, vol. 144, (2012), pp. 1-10.

Ilic, N. et al. "Toxicological evaluation of Grains of Paradise (*Aframomum melegueta*) [Roscoe] K. Schum," Journal of Ethnopharmacology, vol. 127, (2010), pp. 352-356.

Nurtjahja-Tjendraputra, E. et al. "Effective anti-platelet and COX-1 enzyme inhibitors from pungent constituents of ginger," Thrombosis Research, vol. 111, (2003), pp. 259-265.

Umukoro, S. et al. "Further pharmacological studies on aqueous seed extract of Aframomum melegueta in rats," Journal of Ethnopharmacology, vol. 115, (2007) pp. 489-493.

Umukoro, S. et al. "Effects of Aframomum Meleguta Seed Extract on Thermal Pain and Carrageenin-Induced Oedema," Nigerian Quarterly Journal of Hospital Medicine, vol. 11, (2001) pp. 33-35.

Hibino, T. et al., "Goshuyuto, a Traditional Japanese Medicine for Migraine, Inhibits Platelet Aggregation in Guinea-Pig Whole Blood," J. Pharmacological Sciences, vol. 108, No. 1, p. 89-94, (2008).

Guh, J.H. et al., "Antiplatelet effect of gingerol isolated from *Zingiber officinale,*" *The Journal of Pharmacy and Pharmacology*, vol. 47, No. 4, pp. 329-332 (1995).

Yamamoto, K., "Clinical practice of antiplatelet therapy," *The Japanese Journal of Thrombosis and Hemostasis*, vol. 19, 2nd issue, pp. 179-182 (2008).

\* cited by examiner

METHODS FOR REDUCING PLATELET AGGREGATION AND TREATING CARDIOVASCULAR DISEASE AND OTHER MEDICAL DISORDERS

CROSS REFERENCE TO RELATED APPLICATIONS

This application is the national stage of International (PCT) Patent Application Serial No. PCT/US2015/066641, filed Dec. 18, 2015 which claims the benefit of and priority to U.S. Provisional Patent Application Ser. No. 62/094,488, filed Dec. 19, 2014, the contents of each of which are hereby incorporated by reference.

FIELD OF THE INVENTION

The invention provides therapeutic compositions containing ground seed of *Aframomum meleguata* or an extract thereof, and methods for using such compositions to reduce platelet aggregation and treat medical disorders in a patient, such as cardiovascular disease.

BACKGROUND

Platelet aggregation is a contributing factor to cardiovascular disease in a patient. For example, platelet aggregation is involved in unstable angina, acute myocardial infarction, transient ischemic attacks, and a variety of other vaso-occlusive disorders. Platelets can be activated and aggregate when a blood vessel is damaged, such as by acute intervention such as angioplasty or by chronic conditions such as atherosclerosis. Aggregation of platelets can lead to occlusive thrombus formation (blood clots) in blood vessels.

Patients suffering from cardiovascular disease are often instructed to take aspirin as a preventative and/or therapeutic approach to managing their cardiovascular disease, which may include, for example, myocardial infarction, stroke, unstable angina pectoris, chronic angina pectoris, transient ischemic attacks, and congestive heart failure. Low-dose aspirin (e.g., 75 to 100 mg per day orally) can reduce platelet aggregation in patients. However, aspirin has been reported to cause increased bleeding, in particular, gastrointestinal bleeding in patients.

Thus, while aspirin can provide certain benefits by reducing platelet aggregation, aspirin can have significant adverse side effects that are particularly undesirable when the drug is administered chronically to a patient. The need exists for additional therapies for reducing platelet aggregation in a subject and reducing the risk of, or treating, cardiovascular disease. The present invention addresses this need and provides other related advantages.

SUMMARY

The invention provides therapeutic compositions containing ground seed of *Aframomum meleguata* or an extract thereof, therapeutic compositions containing ground seed of *Aframomum meleguata* and rhizome of the plant *Zingiber officinale*, or extracts thereof; and methods for using such compositions to reduce platelet aggregation and treat medical disorders in a patient. Ground seed of *Aframomum meleguata* is commonly referred to as grains of paradise and as *Meleguta* pepper. Rhizome of the plant *Zingiber officinale* is commonly referred to as ginger or ginger root, where *Zingiber officinale* is a perennial reed-like plant with annual leafy stems, indigenous to southern China. The therapeutic compositions provide a benefit when administered to a patient, such as reducing platelet aggregation, treating cardiovascular disease, and reducing the risk of cardiovascular disease. One benefit of the therapeutic composition over an aspirin-based therapy is the therapeutic composition does not cause the magnitude of adverse gastrointestinal side effects (e.g., bleeding) often associated with aspirin therapy. Various aspects and embodiments of the invention are described below.

One aspect of the invention provides a method of treating cardiovascular disease in a patient. The method comprises administering to a patient in need thereof an effective amount of a therapeutic composition described herein to treat the cardiovascular disease. Without being bound by theory, it is understood that the therapeutic compositions provide treatment of cardiovascular disease in a patient by reducing platelet aggregation. An exemplary more specific aspect of the invention provides a method of treating cardiovascular disease in a patient, wherein the method comprises orally administering to a patient in need thereof an effective amount of a therapeutic composition comprising ground seed of *Aframomum meleguata* or an extract thereof, to treat the cardiovascular disease. Exemplary cardiovascular diseases include, for example, acute coronary syndrome, myocardial infarction, stroke, peripheral arterial disease, transient ischemic attack, angina, (e.g., unstable angina pectoris, or chronic stable angina pectoris), or atherosclerosis.

Another aspect of the invention provides a method of reducing the risk of cardiovascular disease in a patient. The method comprises administering to a patient in need thereof an effective amount of a therapeutic composition described herein to reduce the risk of cardiovascular disease. Without being bound by theory, it is understood that the therapeutic compositions reduce the risk of cardiovascular disease in a patient by reducing platelet aggregation. An exemplary more specific aspect of the invention provides a method of reducing the risk of cardiovascular disease in a patient, wherein the method comprises orally administering to a patient in need thereof an effective amount of a therapeutic composition comprising ground seed of *Aframomum meleguata* or an extract thereof, to reduce the risk of cardiovascular disease. Exemplary cardiovascular diseases include, for example, acute coronary syndrome, myocardial infarction, stroke, peripheral arterial disease, transient ischemic attack, angina, (e.g., unstable angina pectoris, or chronic stable angina pectoris), or atherosclerosis.

Another aspect of the invention provides a method of reducing platelet aggregation in a patient. The method comprises administering to a patient in need thereof an effective amount of a therapeutic composition described herein to reduce platelet aggregation. In a more specific aspect, the invention provides a method of reducing platelet aggregation in a patient, wherein the method comprises orally administering to a patient in need thereof an effective amount of a therapeutic composition described herein to reduce platelet aggregation. The reduction in platelet aggregation may be, for example, at least 50%, 75%, or 90%. Another exemplary more specific aspect of the invention provides a method of reducing the incidence of platelet aggregation by at least 40% in a patient, wherein the method comprises orally administering to a patient in need thereof an effective amount of a therapeutic composition comprising ground seed of *Aframomum meleguata* or an extract thereof, to thereby reduce the incidence of platelet aggregation by at least 40% in the patient.

Another aspect of the invention provides a method of treating migraine headache in a patient. The method comprises administering to a patient in need thereof an effective amount of a therapeutic composition described herein to treat the migraine headache. An exemplary more specific aspect of the invention provides a method of treating migraine headache in a patient, wherein the method comprises administering to a patient in need thereof an effective amount of a therapeutic composition comprising ground seed of *Aframomum meleguata* or an extract thereof, to treat the migraine headache.

Another aspect of the invention provides a method of reducing a feature of migraine headache selected from the group consisting of frequency of a migraine headache, duration of a migraine headache, and pain intensity of a migraine headache. The method comprises administering to a patient in need thereof an effective amount of a therapeutic composition described herein to reduce said feature of migraine headache. An exemplary more specific aspect of the invention provides a method of reducing a feature of migraine headache selected from the group consisting of frequency of a migraine headache, duration of a migraine headache, and pain intensity of a migraine headache, wherein the method comprises administering to a patient in need thereof an effective amount of a therapeutic composition comprising ground seed of *Aframomum meleguata* or an extract thereof, to reduce said feature of migraine headache.

Another aspect of the invention provides a method of treating a disorder selected from the group consisting of osteoarthritis, rheumatoid arthritis, ulcer (e.g., an ulcer in the stomach, or a duodenal ulcer), Type II Diabetes, weight loss, menorrhagia, dysmenorrhea, chemotherapy induced nausea or vomiting, an inflammatory disorder (e.g., a neuroinflammatory disorder such as dementia), and pain. The method comprises administering to a patient in need thereof an effective amount of a therapeutic composition described herein (e.g., a therapeutic composition comprising ground seed of *Aframomum meleguata* or an extract thereof), to treat the disorder.

DETAILED DESCRIPTION OF THE INVENTION

The invention provides therapeutic compositions containing ground seed of *Aframomum meleguata* or an extract thereof; therapeutic compositions containing ground seed of *Aframomum meleguata* and rhizome of the plant *Zingiber officinale*, or extracts thereof; and methods for using such compositions to reduce platelet aggregation and treat medical disorders in a patient. Ground seed of *Aframomum meleguata* is commonly referred to as grains of paradise and as *Meleguta* pepper. Rhizome of the plant *Zingiber officinale* is commonly referred to as ginger or ginger root, where *Zingiber officinale* is a perennial reed-like plant with annual leafy stems, indigenous to southern China. The therapeutic compositions provides a benefit when administered to a patient, such as reducing platelet aggregation, treating cardiovascular disease, and reducing the risk of cardiovascular disease. One benefit of the therapeutic composition over an aspirin-based therapy is the therapeutic composition does not cause the magnitude of adverse gastrointestinal side effects (e.g., bleeding) often associated with aspirin therapy. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a therapeutic composition sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "about" means±10% of the stated value, unless specified otherwise. In certain more specific embodiments, "about" a stated value may be ±9%, ±8%, ±7%, ±6%, ±5%, ±3%, ±2%, or ±1% of the stated value.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Therapeutic Compositions

One aspect of the invention provides therapeutic compositions for use in the methods and kits described herein. In one embodiment, the therapeutic composition comprises ground seed of *Aframomum meleguata* or an extract thereof. In certain embodiments, the therapeutic composition comprises (i) ground seed of *Aframomum meleguata* and (ii) an extract thereof of ground seed of *Aframomum meleguata*. In another embodiment, the therapeutic composition comprises (i) ground seed of *Aframomum meleguata*, or an extract thereof, and (ii) rhizome of the plant *Zingiber officinale*, or an extract thereof. The therapeutic compositions are contemplated to provide a benefit when administered to a patient, such as treating cardiovascular disease, reducing the risk of cardiovascular disease, and reducing platelet aggregation. One benefit of the therapeutic composition over an aspirin-based therapy is the therapeutic composition does not cause the magnitude of adverse gastrointestinal side effects (e.g., bleeding) often associated with aspirin therapy.

Ground seed of *Aframomum meleguata* is commonly referred to as grains of paradise and as *Meleguta* pepper. *Aframomum meleguata* is a reed-like plant of the natural order Zingiberaceae, which is native to tropical western Africa.

Rhizome of the plant *Zingiber officinale* is commonly referred to as ginger or ginger root. *Zingiber officinale* is a perennial reed-like plant with annual leafy stems, indigenous to southern China.

Additional embodiments of the therapeutic compositions are described below, and all combinations and permutations of such embodiments are contemplated.

Therapeutic Compositions Containing *Aframomum Meleguata* or an Extract Thereof

One aspect of the invention provides therapeutic compositions comprising ground seed of *Aframomum meleguata* or an extract thereof. In certain embodiments, therapeutic composition comprises ground seed of *Aframomum meleguata*. In certain embodiments, therapeutic composition comprises an extract of ground seed of *Aframomum meleguata*. In certain embodiments, therapeutic composition comprises both ground seed of *Aframomum meleguata* and an extract of ground seed of *Aframomum meleguata*. In yet other embodiments, the therapeutic composition consists of (i) ground seed of *Aframomum meleguata*, an extract thereof, or both, and (b) optionally a pharmaceutically acceptable carrier. In still other embodiments, the therapeutic composition consists of (i) an extract of ground seed of *Aframomum meleguata*, and (b) optionally a pharmaceutically acceptable carrier.

The above compositions may be used in methods for treating cardiovascular disease described herein. In certain embodiments, the therapeutic composition is further characterized by the feature that the ground seed of *Aframomum meleguata* or an extract thereof is the only active ingredient for treating cardiovascular disease in the therapeutic composition. In certain embodiments, the therapeutic composition is further characterized by the feature that the ground seed of *Aframomum meleguata* or an extract thereof is the only active ingredient for treating cardiovascular disease in the therapeutic composition. In certain embodiments, the therapeutic composition is further characterized by the feature that the extract of ground seed of *Aframomum meleguata* is the only active ingredient for treating cardiovascular disease in the therapeutic composition.

The above compositions may be used in methods for reducing the risk of cardiovascular disease described herein. In certain embodiments, the therapeutic composition is further characterized by the feature that the ground seed of *Aframomum meleguata* or an extract thereof is the only active ingredient for reducing the risk of cardiovascular disease in the therapeutic composition. In certain embodiments, the therapeutic composition is further characterized by the feature that the extract of ground seed of *Aframomum meleguata* is the only active ingredient for reducing the risk of cardiovascular disease in the therapeutic composition. In certain embodiments, the therapeutic composition is further characterized by the feature that the therapeutic composition consists of (i) ground seed of *Aframomum meleguata*, an extract thereof, or both, and (b) optionally a pharmaceutically acceptable carrier. In certain embodiments, the therapeutic composition is further characterized by the feature that the therapeutic composition consists of (i) an extract of ground seed of *Aframomum meleguata*, and (b) optionally a pharmaceutically acceptable carrier.

The above compositions may be used in methods for of reducing the incidence of platelet aggregation in a patient (e.g., a reduction by at least 40%) described herein. In certain embodiments, the therapeutic composition is further characterized by the feature that the ground seed of *Aframomum meleguata* or an extract thereof is the only active ingredient for reducing the incidence of platelet aggregation in the therapeutic composition. In certain embodiments, the therapeutic composition is further characterized by the feature that the extract of ground seed of *Aframomum meleguata* is the only active ingredient for reducing the incidence of platelet aggregation in the therapeutic composition. In certain embodiments, the therapeutic composition is further characterized by the feature that the therapeutic composition consists of (i) ground seed of *Aframomum meleguata*, an extract thereof, or both, and (b) optionally a pharmaceutically acceptable carrier. In certain embodiments, the therapeutic composition is further characterized by the feature that the therapeutic composition consists of (i) an extract of ground seed of *Aframomum meleguata*, and (b) optionally a pharmaceutically acceptable carrier.

The above compositions may be used in methods for treating migraine headache or reducing a feature thereof described herein. In certain embodiments, the therapeutic composition is further characterized by the feature that the ground seed of *Aframomum meleguata* or an extract thereof is the only active ingredient for treating migraine headache or reducing a feature thereof in the therapeutic composition. In certain embodiments, the therapeutic composition is further characterized by the feature that the extract of ground seed of *Aframomum meleguata* is the only active ingredient for migraine headache or reducing a feature thereof in the therapeutic composition. In certain embodiments, the therapeutic composition is further characterized by the feature that the therapeutic composition consists of (i) ground seed of *Aframomum meleguata*, an extract thereof, or both, and (b) optionally a pharmaceutically acceptable carrier. In certain embodiments, the therapeutic composition is further characterized by the feature that the therapeutic composition consists of (i) an extract of ground seed of *Aframomum meleguata*, and (b) optionally a pharmaceutically acceptable carrier.

Certain extracts of ground seed of *Aframomum meleguata* have been described in the literature and/or are available from commercial sources, and these extracts of ground seed of *Aframomum meleguata* are contemplated for use in the present methods described herein. See, for example, J. Sugita et al. in *Br. J. Nutr.* (2013) vol. 110(4), pages 733-38; J. Sugita et al. in *J. Nutr. Sci. Vitaminol.* (Tokyo) (2014) vol.

60, pages 22-27; Iwami et al. in *Autonomic Neuroscience* (2011) vol. 161, pages 63-67; an extract of ground seed of *Aframomum meleguata* sold by NutraGreen Biotechnology Co., Ltd. located in Shanghai, China; and an extract of ground seed of *Aframomum meleguata* sold under the tradename Paradoxine™ by Genabolix located in Vancouver, Canada.

Therapeutic Compositions Containing *Aframomum Meleguata*, Rhizome of the Plant *Zingiber Officinale*, and or Extracts of the Foregoing One aspect of the invention provides a therapeutic composition comprising (i) ground seed of *Aframomum meleguata*, or an extract thereof; and (ii) rhizome of the plant *Zingiber officinale*, or an extract thereof. The combination of (i) ground seed of *Aframomum meleguata*, or an extract thereof, and (ii) rhizome of the plant *Zingiber officinale*, or an extract thereof is contemplated to provide a benefit when administered to a patient, such as reducing platelet aggregation and optionally further improving glycemic control, reducing inflammation, and reducing the frequency or magnitude of motion sickness, morning sickness, migraine headache, nausea, or vomiting experienced by the patient. One benefit of the therapeutic composition over an aspirin-based therapy for reduce platelet aggregation is the therapeutic composition does not cause the magnitude of adverse gastrointestinal side effects (e.g., bleeding) often associated with aspirin therapy.

Amount of Components in Therapeutic Compositions Containing *Aframomum Meleguata*. Rhizome of the Plant *Zingiber* Officinale, and or Extracts of the Foregoing The therapeutic composition can be characterized according to the amount of (i) ground seed of *Aframomum meleguata*, or an extract thereof, and (ii) rhizome of the plant *Zingiber officinale*, or an extract thereof. In certain embodiments, the therapeutic composition is characterized by one of the following:

a. comprises from about 10% w/w to about 30% w/w ground seed of *Aframomum meleguata*, or an extract thereof; and from about 70% w/w to about 90% w/w of rhizome of the plant *Zingiber officinale*, or an extract thereof;

b. comprises from about 30% w/w to about 60% w/w ground seed of *Aframomum meleguata*, or an extract thereof; and from about 40% w/w to about 70% w/w of rhizome of the plant *Zingiber officinale*, or an extract thereof; or c. comprises from about 70% w/w to about 90% w/w ground seed of *Aframomum meleguata*, or an extract thereof; and from about 10% w/w to about 30% why of rhizome of the plant *Zingiber officinale*, or an extract thereof.

In certain embodiments, the therapeutic composition corresponds to one of those described in Table 1.

TABLE 1

| Composition No. | Amount of Ground Seed of *Aframomum Meleguata* or Extract Thereof in the Therapeutic Composition (percent by weight) | Amount of Rhizome of the Plant *Zingiber Officinale* or Extract Thereof in the Therapeutic Composition (percent by weight) |
|---|---|---|
| 1 | <5 | >95 |
| 2 | 5-10 | 90-95 |
| 3 | 10-15 | 85-90 |
| 4 | 15-20 | 80-85 |
| 5 | 20-25 | 75-80 |
| 6 | 25-30 | 70-75 |
| 7 | 30-35 | 65-70 |
| 8 | 35-40 | 60-65 |
| 9 | 40-45 | 55-60 |
| 10 | 45-50 | 50-55 |
| 11 | 50-55 | 45-50 |
| 12 | 55-60 | 40-45 |
| 13 | 60-65 | 35-40 |
| 14 | 65-70 | 30-35 |
| 15 | 70-75 | 25-30 |
| 16 | 75-80 | 20-25 |
| 17 | 80-85 | 15-20 |
| 18 | 85-90 | 10-15 |
| 19 | 90-95 | 5-10 |
| 20 | >95 | <5 |

In certain embodiments, it is ground seed of *Aframomum meleguata* and rhizome of the plant *Zingiber officinale* that is present in the therapeutic composition. As such, in certain embodiments, the therapeutic composition is characterized by one of the following:

a. comprises from about 10% w/w to about 30% w/w ground seed of *Aframomum meleguata*; and from about 70% w/w to about 90% w/w of rhizome of the plant *Zingiber officinale*;

b. comprises from about 30% w/w to about 60% w/w ground seed of *Aframomum meleguata*; and from about 40% w/w to about 70% w/w of rhizome of the plant *Zingiber officinale*; or c. comprises from about 70% w/w to about 90% w/w ground seed of *Aframomum meleguata* and from about 10% w/w to about 30% w/w of rhizome of the plant *Zingiber officinale*.

In certain embodiments, the therapeutic composition corresponds to one of those described in Table 2.

TABLE 2

| Composition No. | Amount of Ground Seed of *Aframomum Meleguata* in the Therapeutic Composition (percent by weight) | Amount of Rhizome of the Plant *Zingiber Officinale* in the Therapeutic Composition (percent by weight) |
|---|---|---|
| 1 | <5 | >95 |
| 2 | 5-10 | 90-95 |
| 3 | 10-15 | 85-90 |
| 4 | 15-20 | 80-85 |
| 5 | 20-25 | 75-80 |
| 6 | 25-30 | 70-75 |
| 7 | 30-35 | 65-70 |
| 8 | 35-40 | 60-65 |
| 9 | 40-45 | 55-60 |
| 10 | 45-50 | 50-55 |
| 11 | 50-55 | 45-50 |
| 12 | 55-60 | 40-45 |
| 13 | 60-65 | 35-40 |
| 14 | 65-70 | 30-35 |
| 15 | 70-75 | 25-30 |
| 16 | 75-80 | 20-25 |
| 17 | 80-85 | 15-20 |
| 18 | 85-90 | 10-15 |
| 19 | 90-95 | 5-10 |
| 20 | >95 | <5 |

The therapeutic composition can be characterized according to the ratio of weight percent of (i) ground seed of *Aframomum meleguata* or an extract thereof to (ii) rhizome of the plant *Zingiber officinale* or an extract thereof. In certain embodiments, the ratio of weight percent of (i) ground seed of *Aframomum meleguata* or an extract thereof to (ii) rhizome of the plant *Zingiber officinale* or an extract thereof is one of the following: (a) in the range of from 1:4 to 4:1; (b) in the range of from 1:3 to 3:1, or (c) in the range of from 1:2 to 2:1. In certain embodiments, the ratio of weight percent of (i) ground seed of *Aframomum meleguata* or an extract thereof to (ii) rhizome of the plant *Zingiber officinale* or an extract thereof is one of the following: (a) in the range of from 1:4 to 1:3; (b) in the range of from 1:3 to 1:2; (c) in the range of from 1:2 to 1:1, (d) in the range of from 1:1 to 2:1, (e) in the range of from 2:1 to 3:1, or (f) in the range of from 3:1 to 4:1.

In certain embodiments, the ratio of weight percent of (i) ground seed of *Aframomum meleguata* to (ii) rhizome of the plant *Zingiber officinale* is one of the following: (a) in the range of from 1:4 to 4:1; (b) in the range of from 1:3 to 3:1; or (c) in the range of from 1:2 to 2:1. In certain embodiments, the ratio of weight percent of (i) ground seed of *Aframomum meleguata* to (ii) rhizome of the plant *Zingiber officinale* is one of the following: (a) in the range of from 1:4 to 1:3; (b) in the range of from 1:3 to 1:2; (c) in the range of from 1:2 to 1:1, (d) in the range of from 1:1 to 2:1, (e) in the range of from 2:1 to 3:1, or (f) in the range of from 3:1 to 4:1.

Amount of 6-Paradol in the Therapeutic Composition

The therapeutic composition can be characterized according to the amount of certain components in the composition, such as the amount 6-paradol present in the therapeutic composition. In certain embodiments, the therapeutic composition contains 6-paradol in an amount of:
a. at least 0.1% w/w of the therapeutic composition;
b. at least 1% w/w of the therapeutic composition;
c. at least 2% w/w of the therapeutic composition;
d. at least 4% w/w of the therapeutic composition;
e. at least 6% w/w of the therapeutic composition;
f. at least 8% w/w of the therapeutic composition;
g. at least 10% w/w of the therapeutic composition; or
h. at least 12% w/w of the therapeutic composition.

In certain embodiments, the therapeutic composition contains 6-paradol in an amount of from about 0.1% w/w to about 1% w/w, about 1% w/w to about 2% w/w, about 2% w/w to about 3% w/w, about 3% w/w to about 4% w/w, about 4% w/w to about 5% w/w, about 5% w/w to about 6% w/w, about 6% w/w to about 7% w/w, about 7% w/w to about 8% w/w, about 8% w/w to about 9% w/w, about 9% w/w to about 10% w/w, about 10% w/w to about 11% w/w, about 11% w/w to about 12% w/w, about 4% w/w to about 7% w/w, about 7% w/w to about 10% w/w, or about 10% w/w to about 14% w/w. In certain preferred embodiments, the therapeutic composition contains 6-paradol in an amount of about 10% w/w.

Characterization of the Ground Seed of *Aframomum Meleguata* or Extract Thereof

The ground seed of *Aframomum meleguata* or an extract thereof can be characterized according to the amount of certain components in the ground seed of *Aframomum meleguata* or an extract thereof, such as the amount of 6-paradol present in the ground seed of *Aframomum meleguata* or an extract thereof. In certain embodiments, the ground seed of *Aframomum meleguata* or an extract thereof is characterized by:
a. comprises from about 8% w/w to about 16% w/w 6-paradol;
b. comprises from about 10% w/w to about 16% w/w 6-paradol;
c. comprises from about 10% w/w to about 14% w/w 6-paradol; or
d. comprises from about 12% w/w 6-paradol.

In certain embodiments, the therapeutic composition contains ground seed of *Aframomum meleguata* that is characterized by:
a. comprises from about 8% w/w to about 16% w/w 6-paradol;
b. comprises from about 10% w/w to about 16% w/w 6-paradol;
c. comprises from about 10% w/w to about 14% w/w 6-paradol; or
d. comprises from about 12% w/w 6-paradol.

In certain embodiments, the extract of ground seed of *Aframomum meleguata* is characterized by:
a. comprises from about 8% w/w to about 16% w/w 6-paradol;
b. comprises from about 10% w/w to about 16% w/w 6-paradol;
c. comprises from about 10% w/w to about 14% w/w 6-paradol; or
d. comprises from about 12% w/w 6-paradol.

In certain embodiments, the extract of ground seed of *Aframomum meleguata* contains 6-paradol in an amount of from about 0.1% w/w to about 1% w/w, about 1% why to about 2% w/w, about 2% w/w to about 3% w/w, about 3% w/w to about 4% w/w, about 4% w/w to about 5% w/w, about 5% w/w to about 6% w/w, about 6% w/w to about 7% w/w, about 7% w/w to about 8% w/w, about 8% w/w to about 9% w/w, about 9% w/w to about 10% w/w, about 10% w/w to about 11% w/w, about 11% w/w to about 12% w/w, about 4% w/w to about 7% w/w, about 7% w/w to about 10% w/w, or about 10% w/w to about 14% w/w. In certain preferred embodiments, the extract of ground seed of *Aframomum meleguata* contains 6-paradol in an amount of about 10% w/w.

Characterization of Rhizome of the Plant *Zingiber Officinale* or Extract Thereof Rhizome of the plant *Zingiber officinale* or an extract thereof can be characterized according to the amount of certain components in the rhizome of the plant *Zingiber officinale* or an extract thereof, such as the amount of gingerols present in the rhizome of the plant *Zingiber officinale* or an extract thereof. In certain embodiments, the rhizome of the plant *Zingiber* officinale or an extract thereof is characterized by: (a) comprises from about 4% w/w to about 6% w/w gingerols; or (b) comprises about 5% w/w gingerols. In certain embodiments, the therapeutic composition contains rhizome of the plant *Zingiber offcinale* that is characterized by: (a) comprises from about 4% w/w to about 6% w/w gingerols; or (b) comprises about 5% w/w gingerols.

Therapeutic Composition Containing Ground Seed of *Aframomum Meleguata* or an Extract Thereof as the Only Active Ingredient Another aspect of the invention provides a therapeutic composition comprising ground seed of *Aframomum meleguata* or an extract thereof as the only active ingredient for treating the particular medical disorder. Such therapeutic compositions can be characterized according to, for example, the amount of 6-paradol present in the ground seed of *Aframomum meleguata* or an extract thereof. In certain embodiments, the ground seed of *Aframomum meleguata* or an extract thereof is characterized by:
a. comprises from about 8% w/w to about 16% w/w 6-paradol;

b. comprises from about 10% w/w to about 16% w/w 6-paradol;
c. comprises from about 10% w/w to about 14% w/w 6-paradol; or
d. comprises from about 12% w/w 6-paradol.

In certain other embodiments, the ground seed of *Aframomum meleguata* or an extract thereof is characterized by:
a. comprises from about 8% w/w to about 16% w/w 6-paradol;
b. comprises from about 10% w/w to about 16% w/w 6-paradol;
c. comprises from about 10% w/w to about 14% w/w 6-paradol;
d. comprises from about 10% w/w 6-paradol; or
e. comprises from about 12% w/w 6-paradol.

In certain preferred embodiments, the ground seed of *Aframomum meleguata* or an extract thereof is characterized by comprising from about 8% w/w to about 12% w/w 6-paradol, and more preferably about 10% w/w 6-paradol.

Additional Features of the Therapeutic Composition

The therapeutic composition is preferably formulated for oral administration. The therapeutic composition may also contain a pharmaceutically acceptable carrier. In a preferred embodiment, the therapeutic composition has a pharmaceutically acceptable carrier. Exemplary pharmaceutically acceptable carriers include (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose.

Another aspect of the invention provides a unit dose formulation for oral administration to a patient, where the unit dose formulation comprises a therapeutic composition described herein. Exemplary unit dose formulations for oral administration include capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of a therapeutic composition of the present invention as an active ingredient.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may be sterilized by, for example, filtration through a bacteria-retaining filter, or by incorporating sterilizing agents in the form of sterile solid compositions which can be dissolved in sterile water, or some other sterile injectable medium immediately before use.

Besides inert diluents, the oral compositions can also include adjuvants such as wetting agents, emulsifying and suspending agents, sweetening, flavoring, coloring, perfuming and preservative agents.

III. Therapeutic Applications

The invention provides methods of reducing platelet aggregation and treating medical disorders, such as cardiovascular disease and migraine headache, using the therapeutic compositions described herein. Treatment methods include the use of the therapeutic compositions described herein as stand-alone agents and/or as part of a combination therapy with another therapeutic agent. Various aspects and embodiments of the therapeutic methods are described below, and all combinations and permutations of embodiments are contemplated.

Part A—Methods of Reducing Platelet Aggregation

One aspect of the invention provides a method of reducing platelet aggregation in a patient. The method comprises orally administering to a patient in need thereof an effective amount of a therapeutic composition described herein, such as in Section II, to reduce platelet aggregation. Reducing platelet aggregation provides numerous health benefits to patients, particularly those patients at risk for or suffering from cardiovascular disease. Various embodiments of the method are described below, and all combinations and permutations of such embodiments are contemplated.

Extent of Reduction in Platelet Aggregation

The method can be characterized according to the extent to which platelet aggregation is reduced. For example, in certain embodiments, the method is characterized by achieving a reduction in platelet aggregation in the patient of: at least 10%, at least 25%, at least 40%, or at least 55%. In certain other embodiments, the method is characterized by achieving a reduction in platelet aggregation in the patient of: at least 60%, at least 75%, at least 85%/6, or at least 90%.

The method can be also characterized according to the duration of time over which a reduction in platelet aggregation is achieved following a single administration of the therapeutic composition. In certain embodiments, a single daily administration of said therapeutic composition achieves said reduction in platelet aggregation in the patient for a duration of at least 1, 2, 3, 4, 5, 6, 7, 8, 9, 10, 12, 14, 16, 18, 20, 24, 28, 30, 36, 40, 45, 50, 55, 60, 70, 80, or 90 hours. In certain embodiments, a single daily administration of said therapeutic composition achieves said reduction in platelet aggregation in the patient for a duration of at least 5 hours. In certain embodiments, a single daily administration of said therapeutic composition achieves said reduction in platelet aggregation in the patient for a duration of at least 36 hours.

Platelet aggregation can be analyzed according to procedures described in the literature, such as in Shih et al. in *Int. J. Mol. Sci* (2014) vol. 15, pages 3926-395 1and Koo et al. in *Thomb Res* (2001) vol. 103, pages 387-98, which is hereby incorporated by reference.

Exemplar More Specific Method for Reducing Platelet Aggregation

An exemplary more specific aspect of the invention provides a method of reducing the incidence of platelet aggregation by at least 40% in a patient, wherein the method comprises orally administering to a patient in need thereof an effective amount of a therapeutic composition comprising ground seed of *Aframomum meleguata* or an extract thereof, to thereby reduce the incidence of platelet aggregation by at least 40% in the patient.

In certain embodiments, there is a reduction in the incidence of platelet aggregation caused by arachidonic acid, there is a reduction in the incidence of platelet aggregation caused by adenosine diphosphate, and there is a reduction in the incidence of platelet aggregation caused by collagen.

In certain embodiments, the method may be further characterized by achieving a reduction in the incidence of platelet aggregation by at least 55% in the patient. In certain embodiments, the method may be further characterized by achieving a reduction in the incidence of platelet aggregation in the patient of:

a. at least 60%;
b. at least 75%;
c. at least 85%; or
d. at least 90%.

In certain embodiments, the method may be further characterized by the feature that a single daily administration of said therapeutic composition achieves said reduction in the incidence of platelet aggregation in the patient for a duration of at least 5 hours. In certain other embodiments, the method may be further characterized by the feature that a single daily administration of said therapeutic composition achieves said reduction in the incidence of platelet aggregation in the patient for a duration of at least 36 hours. In certain other embodiments, the method may be further characterized by the feature that a single daily administration of said therapeutic composition achieves said reduction in the incidence of platelet aggregation in the patient for a duration of at least 2 days, 3 days, 4 days, 5 days, or 6 days.

Part B—Methods of Treating Cardiovascular Medical Disorders

Another aspect of the invention provides a method of reducing the risk of cardiovascular disease in a patient. The method comprises administering to a patient in need thereof an effective amount of a therapeutic composition described herein to reduce the risk of cardiovascular disease. Exemplary cardiovascular diseases include, for example, acute coronary syndrome, myocardial infarction, stroke, peripheral arterial disease, transient ischemic attack, angina, (e.g., unstable angina pectoris, or chronic stable angina pectoris), and atherosclerosis. In certain embodiments, the cardiovascular disease is acute coronary syndrome, myocardial infarction, stroke, peripheral arterial disease, transient ischemic attack, unstable angina pectoris, or chronic stable angina pectoris. In certain embodiments, the cardiovascular disease is acute coronary syndrome, myocardial infarction, or stroke.

Without being bound by theory, it is understood that the therapeutic compositions, such as those described in Section II, reduce the risk of cardiovascular disease in a patient by reducing platelet aggregation. Various embodiments of the method are described below, and all combinations and permutations of such embodiments are contemplated.

Another aspect of the invention provides a method of treating cardiovascular disease in a patient. The method comprises administering to a patient in need thereof an effective amount of a therapeutic composition described herein to treat the cardiovascular disease. Exemplary cardiovascular diseases include, for example, acute coronary syndrome, myocardial infarction, stroke, peripheral arterial disease, transient ischemic attack, angina, (e.g., unstable angina pectoris, or chronic stable angina pectoris), and atherosclerosis. In certain embodiments, the cardiovascular disease is acute coronary syndrome, myocardial infarction, stroke, peripheral arterial disease, transient ischemic attack, unstable angina pectoris, or chronic stable angina pectoris. In certain embodiments, the cardiovascular disease is acute coronary syndrome, myocardial infarction, or stroke.

Without being bound by theory, it is understood that the therapeutic compositions, such as those described in Section II, treat cardiovascular disease in a patient by reducing platelet aggregation. Various embodiments of the method are described below, and all combinations and permutations of such embodiments are contemplated.

Exemplary More Specific Method for Reducing the Risk of Cardiovascular Disease

An exemplary more specific aspect of the invention provides a method of reducing the risk of cardiovascular disease in a patient, wherein the method comprises orally administering to a patient in need thereof an effective amount of a therapeutic composition comprising ground seed of *Aframomum meleguata* or an extract thereof, to reduce the risk of cardiovascular disease.

The method may be further characterized by, for example, the risk of cardiovascular disease is reduced for a duration of at least 1 week, 1 month, 3 months, or 6 months. In certain embodiments, the method achieves a reduction in the incidence of cardiovascular disease by at least 20%, 30%, 40%, 50%, 60%, 70% 80% or 90% in a population of patients that receive the therapeutic composition relative to a medically analogous population of patients that do not receive the therapeutic composition.

The method may be further characterized by, for example, the identity of the cardiovascular disease. In certain embodiments, the cardiovascular disease is acute coronary syndrome, myocardial infarction, stroke, peripheral arterial disease, transient ischemic attack, angina, (e.g., unstable angina pectoris, or chronic stable angina pectoris), or atherosclerosis. In certain embodiments, the cardiovascular disease is acute coronary syndrome, myocardial infarction, stroke, peripheral arterial disease, transient ischemic attack, unstable angina pectoris, or chronic stable angina pectoris. In certain embodiments, the cardiovascular disease is acute coronary syndrome. In certain embodiments, the cardiovascular disease is myocardial infarction. In certain embodiments, the cardiovascular disease is stroke. In certain embodiments, the cardiovascular disease is peripheral arterial disease. In certain embodiments, the cardiovascular disease is transient ischemic attack. In certain embodiments, the cardiovascular disease is angina. In certain embodiments, the cardiovascular disease is unstable angina pectoris. In certain embodiments, the cardiovascular disease is chronic stable angina pectoris. In certain embodiments, the cardiovascular disease is atherosclerosis.

The method may be further characterized according to a concomitant reduction in the incidence of platelet aggregation. For example, in certain embodiments, the method may be further characterized by a reduction in the incidence of platelet aggregation caused by arachidonic acid, a reduction in the incidence of platelet aggregation caused by adenosine diphosphate, and/or a reduction in the incidence of platelet aggregation caused by collagen. In certain embodiments, the method may be further characterized by achieving a reduction in the incidence of platelet aggregation by at least 55% in the patient. In certain embodiments, the method may be further characterized by achieving a reduction in the incidence of platelet aggregation in the patient of:
 a. at least 60%;
 b. at least 75%;
 c. at least 85%; or
 d. at least 90%.

In certain embodiments, the method may be further characterized by the feature that a single daily administration of said therapeutic composition achieves said reduction in the incidence of platelet aggregation in the patient for a duration of at least 5 hours. In certain other embodiments, the method may be further characterized by the feature that a single daily administration of said therapeutic composition achieves said reduction in the incidence of platelet aggregation in the patient for a duration of at least 36 hours. In certain other embodiments, the method may be further characterized by the feature that a single daily administration of said therapeutic composition achieves said reduction in the incidence of platelet aggregation in the patient for a duration of at least 2 days, 3 days, 4 days, 5 days, or 6 days.

Exemplary More Specific Method for Treating Cardiovascular Disease

An exemplary more specific aspect of the invention provides a method of treating cardiovascular disease in a patient, wherein the method comprises orally administering to a patient in need thereof an effective amount of a therapeutic composition comprising ground seed of *Aframomum meleguata* or an extract thereof, to treat the cardiovascular disease.

The method may be further characterized by, for example, the identity of the cardiovascular disease. In certain embodiments, the cardiovascular disease is acute coronary syndrome, myocardial infarction, stroke, peripheral arterial disease, transient ischemic attack, angina, (e.g., unstable angina pectoris, or chronic stable angina pectoris), or atherosclerosis. In certain embodiments, the cardiovascular disease is acute coronary syndrome, myocardial infarction, stroke, peripheral arterial disease, transient ischemic attack, unstable angina pectoris, or chronic stable angina pectoris. In certain embodiments, the cardiovascular disease is acute coronary syndrome. In certain embodiments, the cardiovascular disease is myocardial infarction. In certain embodiments, the cardiovascular disease is stroke. In certain embodiments, the cardiovascular disease is peripheral arterial disease. In certain embodiments, the cardiovascular disease is transient ischemic attack. In certain embodiments, the cardiovascular disease is angina. In certain embodiments, the cardiovascular disease is unstable angina pectoris. In certain embodiments, the cardiovascular disease is chronic stable angina pectoris. In certain embodiments, the cardiovascular disease is atherosclerosis.

The method may be further characterized according to a concomitant reduction in the incidence of platelet aggregation. For example, in certain embodiments, the method may be further characterized by a reduction in the incidence of platelet aggregation caused by arachidonic acid, a reduction in the incidence of platelet aggregation caused by adenosine diphosphate, and/or a reduction in the incidence of platelet aggregation caused by collagen. In certain embodiments, the method may be further characterized by achieving a reduction in the incidence of platelet aggregation by at least 55% in the patient. In certain embodiments, the method may be further characterized by achieving a reduction in the incidence of platelet aggregation in the patient of:
 a. at least 60%;
 b. at least 75%;
 c. at least 85%; or
 d. at least 90%.

In certain embodiments, the method may be further characterized by the feature that a single daily administration of said therapeutic composition achieves said reduction in the incidence of platelet aggregation in the patient for a duration of at least 5 hours. In certain other embodiments, the method may be further characterized by the feature that a single daily administration of said therapeutic composition achieves said reduction in the incidence of platelet aggregation in the patient for a duration of at least 36 hours. In certain other embodiments, the method may be further characterized by the feature that a single daily administration of said therapeutic composition achieves said reduction in the incidence of platelet aggregation in the patient for a duration of at least 2 days, 3 days, 4 days, 5 days, or 6 days.

Part C—Additional Features of Methods from Parts A and B

The methods described above can be further characterized according to dosage, dosing frequency, impact on gastrointestinal tract, contra-indicated patient populations, and additional benefits provided by the therapy.

Dosage

The methods can be further characterized according to the unit dosage of therapeutic composition administered to the patient. The size of the unit dosage can be important for orally administered dosage forms, where the size of the tablet can impact ability of certain patients to consume the dosage form. In certain embodiments, a unit dosage of the therapeutic composition has a mass in the range of: up to 3 g, up to 2 g, up to 1 g, or up to 0.5 g. In yet other embodiments a unit dosage of the therapeutic composition has a mass in the range of:
 a. from about 0.1 g to about 3 g;
 b. from about 0.1 g to about 1 g;
 c. from about 0.5 g to about 1.5 g;
 d. from about 1 g to about 2 g;
 e. from about 1.5 g to about 2.5 g; or
 f. from about 2 g to about 3 g.

The methods can be further characterized according to the daily dosage of therapeutic composition administered to the patient. In certain embodiments, the therapeutic composition is administered at a daily dosage in the range of: (a) up to 3 g per day. (b) up to 2 g per day, or (c) up to 1 g per day. In certain other embodiments, the therapeutic composition is administered at a daily dosage in the range of:
 a. from about 0.1 g to about 3 g per day;
 b. from about 0.1 g to about 1 g per day;
 c. from about 0.5 g to about 1.5 g per day;
 d. from about 1 g to about 2 g per day;
 e. from about 1.5 g to about 2.5 g per day; or
 f. from about 2 g to about 3 g per day.

Of course, actual dosage levels of the therapeutic compositions may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular therapeutic composition of the present invention employed, the time of administration, the duration of the treatment, other drugs, compounds and/or materials used in combination with the particular therapeutic composition employed, the age, sex, weight, condition, general health and prior medical history of the patient being treated, and like factors well known in the medical arts.

Dosing Frequency

The methods can be further characterized according to the frequency at which the therapeutic composition is administered to the patient. In certain embodiments, the therapeutic composition is administered orally once per day. In certain other embodiments, the therapeutic composition is administered orally at least twice per day.

In yet other embodiments, the method is characterized according to the frequency with which the patient receives a unit dosage of the therapeutic composition. For example, in certain embodiments, a unit dosage of the therapeutic composition is orally administered once per day. In certain embodiments, a unit dosage of the therapeutic composition is orally administered once per day for at least 3 days each week. In certain embodiments, a unit dosage of the therapeutic composition is orally administered once per day for at least 5 days each week. In certain embodiments, a unit dosage of the therapeutic composition is orally administered once per day for at least 1 week. In certain embodiments, a unit dosage of the therapeutic composition is orally administered once per day for at least 2 weeks. In certain embodiments, a unit dosage of the therapeutic composition is orally administered once per day for at least 4, 6, 8, 10, 12, 14, 16, or 18 weeks. In certain embodiments, a unit dosage of the therapeutic composition is orally administered one to three times per day. In certain embodiments, a unit dosage of the therapeutic composition is orally administered one to three times per day for at least 3 days each week. In certain embodiments, a unit dosage of the therapeutic composition is orally administered one to three times per day for at least 5 days each week. In certain embodiments, a unit dosage of the therapeutic composition is orally administered one to three times per day for at least 1 week. In certain embodiments, a unit dosage of the therapeutic composition is orally administered one to three times per day for at least 2 weeks. In certain embodiments, a unit dosage of the therapeutic composition is orally administered one to three times per day for at least 4, 6, 8, 10, 12, 14, 16, or 18 weeks. In certain embodiments, a unit dosage of the therapeutic composition is orally administered orally at least twice per day.

Further, if desired, the effective daily dose of the therapeutic composition may be administered as two, three, four, five, six or more sub-doses administered separately at appropriate intervals throughout the day, optionally, in unit dosage forms. Preferred dosing is one administration per day.

Impact on Gastrointestinal Tract

One contemplated benefit of the therapeutic composition is that it produces less gastrointestinal distress than aspirin administered orally at dosages approved by the United States Food and Drug Administration. In certain embodiments, the administering produces less gastric bleeding than aspirin administered orally at a dosage sufficient to achieve the reduction of platelet aggregation achieved using said therapeutic composition.

In certain embodiments, the administering produces at least 50% less (or even at least 60%, 70%, 80%, or 90% less) gastric bleeding than said aspirin administration. In certain embodiments, the gastric bleeding is intestinal bleeding. In certain embodiments, the gastric bleeding is stomach bleeding.

In certain embodiments, the gastrointestinal distress is stomach ulcers. In certain embodiments, a benefit of the therapeutic composition is that is produces fewer ulcers, or ulcers that are smaller in size relative to that observed using aspirin administered orally at dosages approved by the United States Food and Drug Administration.

Contra-Indicated Patient Populations

The methods may be further characterized according to patients not to receive the therapeutic composition. For example, in certain embodiments, patients already receiving a blood thinning medication are selected for exclusion. As such, in certain embodiments, the methods are further characterized by the feature that the patient is not on a treatment regimen involving administration of a blood thinning medication.

Additional Benefits of the Therapeutic Methods

Another contemplated benefit of the therapeutic composition is that it improves glycemic control in the patient. In certain embodiments, the methods are further characterized by achieving at least a 25%, 50%, 75%, or 100% improvement in glycemic control in the patient.

Another contemplated benefit of the therapeutic composition is that it reduces inflammation in the patient. In certain embodiments, the methods are further characterized by achieving at least a 25%, 50%, 75%, or 100% reduction in least one type of inflammation (e.g., a form of joint inflammation) in the patient.

Still other contemplated benefits of the therapeutic composition include reducing the frequency or magnitude of motion sickness, morning sickness, migraine headache, nausea, or vomiting experienced by the patient. Accordingly, in certain embodiments, the methods are further characterized by reducing the frequency or magnitude of motion sickness, morning sickness, migraine headache, nausea, or vomiting experienced by the patient.

Part D—Methods of Treating Migraine Headache & Other Disorders

Another aspect of the invention pertains to methods of treating migraine headache. The therapeutic methods embrace acute treatment of migraine headache as well as prevention of migraine headache. Various embodiments of the methods are described below, and all combinations and permutations of such embodiments are contemplated.

One aspect of the invention provides a method of treating migraine headache in a patient. The method comprises administering to a patient in need thereof an effective amount of a therapeutic composition described herein to treat the migraine headache.

Another aspect of the invention provides a method of reducing a feature of migraine headache selected from the group consisting of frequency of a migraine headache, duration of a migraine headache, and pain intensity of a migraine headache. The method comprises administering to a patient in need thereof an effective amount of a therapeutic composition described herein to reduce said feature of migraine headache.

In certain embodiments, the method comprises preventing migraine headache in a patient. The method comprises administering to a patient in need thereof an effective amount of a therapeutic composition described herein to prevent (e.g., reduce the frequency of) migraine headache.

Another aspect of the invention provides a method of treating disorder selected from the group consisting of osteoarthritis, rheumatoid arthritis, ulcer (e.g., an ulcer in the stomach, or a duodenal ulcer), Type 11 Diabetes, weight loss, menorrhagia, dysmenorrhea, chemotherapy induced nausea or vomiting, an inflammatory disorder (e.g., a neuroinflammatory disorder such as dementia), and pain. The method comprises administering to a patient in need thereof an effective amount of a therapeutic composition described herein (e.g., a therapeutic composition comprising ground seed of *Aframomum meleguata* or an extract thereof), to treat the disorder.

Another aspect of the invention provides a method of improving glycemic control in a patient. The method comprises administering to a patient in need thereof an effective amount of a therapeutic composition described herein (e.g., a therapeutic composition comprising ground seed of *Aframomum meleguata* or an extract thereof), to improve glycemic control. In certain embodiments, the method is characterized by achieving at least a 25%, 50%, 75%, or 100% improvement in glycemic control in the patient.

Additional Features

The methods described above can be further characterized according to dosage, dosing frequency, impact on gastrointestinal tract, contra-indicated patient populations, and additional benefits provided by the therapy.

Dosage

The methods can be further characterized according to the dosage of therapeutic composition administered to the patient. In certain embodiments, dosage of therapeutic composition administered to the patient. In certain embodiments, the therapeutic composition is administered at a daily dosage in the range of: (a) up to 3 g per day, (b) up to 2 g per day, or (c) up to 1 g per day. In certain other embodiments, the therapeutic composition is administered at a daily dosage in the range of:
 a. from about 0.1 g to about 3 g per day;
 b. from about 0.1 g to about 1 g per day;
 c. from about 0.5 g to about 1.5 g per day;
 d. from about 1 g to about 2 g per day;
 e. from about 1.5 g to about 2.5 g per day, or
 f. from about 2 g to about 3 g per day.

Of course, actual dosage levels of the therapeutic compositions may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular therapeutic composition of the present invention employed, the time of administration, the duration of the treatment, other drugs, compounds and/or materials used in combination with the particular therapeutic composition employed, the age, sex, weight, condition, general health and prior medical history of the patient being treated, and like factors well known in the medical arts.

Desirably the therapeutic composition is administered orally. Other modes of administration include, for example, injection and transdermal administration of the therapeutic composition.

Dosing Frequency

The methods can be further characterized according to the frequency at which the therapeutic composition is administered to the patient. In certain embodiments, the therapeutic composition is administered orally once per day. In certain other embodiments, the therapeutic composition is administered orally at least twice per day.

Further, if desired, the effective daily dose of the therapeutic composition may be administered as two, three, four, five, six or more sub-doses administered separately at appropriate intervals throughout the day, optionally, in unit dosage forms. Preferred dosing is one administration per day.

Impact on Gastrointestinal Tract

One contemplated benefit of the therapeutic composition is that it produces less gastrointestinal distress than aspirin administered orally at dosages approved by the United States Food and Drug Administration. In certain embodiments, the administering produces less gastric bleeding than aspirin administered orally at a dosage sufficient to achieve an equivalent effect on migraine heachache in the patient.

In certain embodiments, the administering produces at least 50% less (or even at least 60%, 70%, 80%, or 90% less) gastric bleeding than said aspirin administration. In certain embodiments, the gastric bleeding is intestinal bleeding. In certain embodiments, the gastric bleeding is stomach bleeding.

Contra-Indicated Patient Populations

The methods may be further characterized according to patients not to receive the therapeutic composition. For example, in certain embodiments, patients already receiving a blood thinning medication are selected for exclusion. As such, in certain embodiments, the methods are further characterized by the feature that the patient is not on a treatment regimen involving administration of a blood thinning medication.

Additional Benefits of the Therapeutic Methods

Another contemplated benefit of the therapeutic composition is that it improves glycemic control in the patient. In certain embodiments, the methods are further characterized by achieving at least a 25%, 50%, 75%, or 100% improvement in glycemic control in the patient.

Another contemplated benefit of the therapeutic composition is that it reduces inflammation in the patient. In certain embodiments, the methods are further characterized by achieving at least a 25%, 50%, 75%, or 100% reduction in least one type of inflammation (e.g., a form of joint inflammation) in the patient.

Exemplary More Specific Method for Treating Migraine Headache and Reducing Features Thereof An exemplary more specific aspect of the invention provides a method of treating migraine headache in a patient, wherein the method comprises administering to a patient in need thereof an effective amount of a therapeutic composition comprising ground seed of *Aframomum meleguata* or an extract thereof, to treat the migraine headache.

Another exemplary more specific aspect of the invention provides a method of reducing a feature of migraine headache selected from the group consisting of frequency of a migraine headache, duration of a migraine headache, and pain intensity of a migraine headache, comprising administering to a patient in need thereof an effective amount of a therapeutic composition comprising ground seed of *Aframomum meleguata* or an extract thereof, to reduce said feature of migraine headache.

Part E—Combination Therapy

As indicated above, invention embraces combination therapy, which includes the administration of a therapeutic composition and a second agent as part of a specific treatment regimen intended to provide the beneficial effect from the co-action of these materials. The beneficial effect of the combination may include pharmacokinetic or pharmacodynamic co-action resulting from the combination of these materials.

In certain embodiments, the method further comprises administering a second agent that reduces platelet aggregation in a patient. In certain embodiments, the second agent is clopidogrel, apixaban, ticagrelor, rivaroxaban, or a pharmaceutically acceptable salt thereof.

IV. Kits for Use in Medical Applications

Another aspect of the invention provides a kit for reducing platelet aggregation and/or treating a disorder. The kit comprises: i) instructions for reducing platelet aggregation and/or treating a medical disorder, such as cardiovascular disease or migraine headache; and ii) a therapeutic composition described herein. The kit may comprise one or more unit dosage forms containing an amount of a therapeutic composition described herein.

V. Combinations

The description above describes multiple aspects and embodiments of the invention, including therapeutic compositions containing ground seed of *Aframomum meleguata* or an extract thereof; therapeutic compositions containing ground seed of *Aframomum meleguata* and rhizome of the plant *Zingiber officinale* or extracts of the foregoing; methods of using the therapeutic composition; and kits. The patent application specifically contemplates all combinations and permutations of the aspects and embodiments.

For example, the patent application contemplates the embodiments set forth below:

1. A therapeutic composition comprising:
   (i) ground seed of *Aframomum meleguata*, or an extract thereof; and
   (ii) rhizome of the plant *Zingiber officinale*, or an extract thereof.
2. The therapeutic composition of embodiment 1, wherein the therapeutic composition is characterized by one of the following:
   a. comprises from about 10% w/w to about 30% w/w ground seed of *Aframomum meleguata*, or an extract thereof; and from about 70% w/w to about 90% w/w of rhizome of the plant *Zingiber officinale*, or an extract thereof;
   b. comprises from about 30% w/w to about 60% w/v ground seed of *Aframomum meleguata*, or an extract thereof; and from about 40% w/w to about 70% why of rhizome of the plant *Zingiber offcinale*, or an extract thereof; or
   c. comprises from about 70% w/w to about 90% w/w ground seed of *Aframomum meleguata*, or an extract thereof; and from about 10% w/w to about 30% w/w of rhizome of the plant *Zingiber officinale*, or an extract thereof.
3. The therapeutic composition of embodiment 1, wherein the therapeutic composition is characterized by one of the following:
   a. comprises from about 10% w/w to about 30% w/w ground seed of *Aframomum meleguata*; and from about 70% w/w to about 90% w/w of rhizome of the plant *Zingiber officinale*;
   b. comprises from about 30% w/w to about 60% why ground seed of *Aframomum meleguata*; and from about 40% w/w to about 70% w/w of rhizome of the plant *Zingiber officinale*; or
   c. comprises from about 70% w/w to about 90% w/w ground seed of *Aframomum meleguata*; and from about 10% w/w to about 30% w/w of rhizome of the plant *Zingiber officinale*.
4. The therapeutic composition of embodiment 1, wherein the ratio of weight percent of (i) ground seed of *Aframomum meleguata* or an extract thereof to (ii) rhizome of the plant *Zingiber officinale* or an extract thereof is one of the following:
   a. in the range of from 1:4 to 4:1;
   b. in the range of from 1:3 to 3:1; or
   c. in the range of from 1:2 to 2:1.
5. The therapeutic composition of any one of embodiments 1-4, wherein the ground seed of *Aframomum meleguata* or an extract thereof is characterized by:
   a. comprises from about 8% w/w to about 16% w/w 6-paradol;
   b. comprises from about 10% w/w to about 16% w/w 6-paradol;
   c. comprises from about 10% w/w to about 14% w/w 6-paradol; or
   d. comprises from about 12% w/w 6-paradol.
6. The therapeutic composition of any one of embodiments 1-5, wherein the rhizome of the plant *Zingiber offcinale* or an extract thereof is characterized by:
   a. comprises from about 4% w/w to about 6% w/w gingerols; or
   b. comprises about 5% w/w gingerols.
7. The therapeutic composition of any one of embodiments 1-6, wherein the therapeutic composition contains 6-paradol in an amount of:
   a. at least 0.1% w/w of the therapeutic composition;
   b. at least 1% w/w of the therapeutic composition;
   c. at least 2% w/w of the therapeutic composition;
   d. at least 4% w/w of the therapeutic composition;
   e. at least 6% w/w of the therapeutic composition;
   f. at least 8% w/w of the therapeutic composition;
   g. at least 10% w/w of the therapeutic composition, or
   h. at least 12% w/w of the therapeutic composition.
8. The therapeutic composition of any one of embodiments 1-7, further comprising a pharmaceutically acceptable carrier.
9. The therapeutic composition of any one of embodiments 1-8, formulated for oral administration.
10. A unit dose formulation for oral administration to a patient, comprising a therapeutic composition of any one of embodiments 1-9.
11. A method of reducing platelet aggregation in a patient, comprising orally administering to a patient in need thereof an effective amount of a therapeutic composition of any one of embodiments 1-9 to reduce platelet aggregation.
12. The method of embodiment 1, characterized by achieving a reduction in platelet aggregation in the patient of:
    a. at least 10%;
    b. at least 25%;
    c. at least 40%; or
    d. at least 55%.
13. The method of embodiment 11, characterized by achieving a reduction in platelet aggregation in the patient of:
    a. at least 60%;
    b. at least 75%;
    c. at least 85%; or
    d. at least 90%.
14. The method of any one of embodiments 11-13, wherein a single daily administration of said therapeutic composition achieves said reduction in platelet aggregation in the patient for a duration of at least 5 hours.
15. The method of any one of embodiments 11-14, wherein a single daily administration of said therapeutic composition achieves said reduction in platelet aggregation in the patient for a duration of at least 36 hours.
16. A method of reducing the risk of cardiovascular disease in a patient, comprising administering to a patient in need thereof an effective amount of a therapeutic composition of any one of embodiments 1-9 to reduce the risk of cardiovascular disease.
17. A method of treating cardiovascular disease in a patient, comprising administering to a patient in need thereof an effective amount of a therapeutic composition of any one of embodiments 1-9 to treat the cardiovascular disease.

18. The method of embodiment 16 or 17, wherein the cardiovascular disease is acute coronary syndrome, myocardial infarction, stroke, peripheral arterial disease, transient ischemic attack, unstable angina pectoris, or chronic stable angina pectoris.
19. The method of embodiment 16 or 17, wherein the cardiovascular disease is acute coronary syndrome, myocardial infarction, or stroke.
20. The method of any one of embodiments 11-19, wherein the therapeutic composition is administered at a daily dosage in the range of:
    a. up to 3 g per day;
    b. up to 2 g per day; or
    c. up to 1 g per day.
21. The method of any one of embodiments 11-19, wherein the therapeutic composition is administered at a daily dosage in the range of:
    a. from about 0.1 g to about 3 g per day;
    b. from about 1.0 g to about 1 g per day;
    c. from about 0.5 g to about 1.5 g per day;
    d. from about 1 g to about 2 g per day;
    e. from about 1.5 g to about 2.5 g per day; or
    f. from about 2 g to about 3 g per day.
22. The method of any one of embodiments 11-21, wherein the therapeutic composition is administered orally once per day.
23. The method of any one of embodiments 11-21, wherein the therapeutic composition is administered orally at least twice per day.
24. The method of any one of embodiments 11-23, wherein the administering produces less gastric bleeding than aspirin administered orally at a dosage sufficient to achieve the reduction of platelet aggregation achieved using said therapeutic composition.
25. The method of embodiment 24, wherein said administering produces at least 50% less gastric bleeding than said aspirin administration.
26. The method of embodiment 24 or 25, wherein said gastric bleeding is intestinal bleeding.
27. The method of embodiment 24 or 25, wherein said gastric bleeding is stomach bleeding.
28. The method of any one of embodiments 11-27, wherein the patient is not on a treatment regimen involving administration of a blood thinning medication.
29. The method of any one of embodiments 11-27, further comprising administering a second agent that reduces platelet aggregation in a patient.
30. The method of embodiment 29, wherein the second agent is clopidogrel, apixaban, ticagrelor, rivaroxaban, or a pharmaceutically acceptable salt thereof.
31. The method of any one of embodiments 11-30, wherein the administering improves glycemic control in the patient.
32. The method of any one of embodiments 11-31, wherein the administering reduces inflammation in the patient.
33. The method of any one of embodiments 11-32, wherein the administering reduces the frequency or magnitude of motion sickness, morning sickness, migraine headache, nausea, or vomiting experienced by the patient.
34. A method of treating migraine headache in a patient, comprising administering to a patient in need thereof an effective amount of a therapeutic composition of any one of embodiments 1-9 to treat the migraine headache.
35. A method of reducing a feature of migraine headache selected from the group consisting of frequency of a migraine headache, duration of a migraine headache, and pain intensity of a migraine headache, comprising administering to a patient in need thereof an effective amount of a therapeutic composition of any one of embodiments 1-9 to reduce said feature of migraine headache.
36. The method of embodiment 34 or 35, wherein the therapeutic composition is administered at a daily dosage in the range of:
    a. up to 3 g per day;
    b. up to 2 g per day; or
    c. up to 1 g per day.
37. The method of embodiment 34 or 35, wherein the therapeutic composition is administered at a daily dosage in the range of:
    a. from about 0.1 g to about 3 g per day;
    b. from about 0.1 g to about 1 g per day;
    c. from about 0.5 g to about 1.5 g per day;
    d. from about 1 g to about 2 g per day;
    e. from about 1.5 g to about 2.5 g per day; or
    f. from about 2 g to about 3 g per day.
38. The method of any one of embodiments 34-37, wherein the therapeutic composition is administered orally once per day.
39. The method of any one of embodiments 34-37, wherein the therapeutic composition is administered orally at least twice per day.
40. The method of any one of embodiments 11-39, wherein the patient is a human.

EXAMPLES

The invention now being generally described, will be more readily understood by reference to the following example, which is included merely for purposes of illustration of certain aspects and embodiments of the present invention, and is not intended to limit the invention.

Example 1—Analysis of Ability to Inhibit Platelet Aggregation

The ability of multiple materials to inhibit platelet aggregation was evaluated according to the procedures described below. The analysis evaluated ability of aspirin, 6-paradol, a Grains of Paradise Extract, a Ginger Extract, and a Ginger Extract spiked with 6-paradol to inhibit platelet aggregation induced by arachidonic acid, adenosine diphosphate, or collagen. Results are provided below.

I. Equipment and Materials

The following list describes equipment and materials used in this study:
1. Light Transmission Aggregometer (Chrono-log, Model #700)
2. Centrifuge (Sorvall RT-1)
3. Cell Counter (Horiba, Model #Micros 60)
4. Waterbath (Isotemp, Model #2340)
5. Arachidonic Acid (BioData, Cat #101297, Lot #06700070A)
6. Adenosine Diphosphate (ADP) (Sigma. Cat #A2754, Lot #SLBB1854V)
7. Collagen (Chronolog, Ref #385, Lot #3440)
8. Dimethylsulfoxide (DMSO) (Sigma. Ref #D2650. Lot #RNBC9664)
9. Saline (CirQuest, Lot #22 Jul. 2014)
10. Ethanol (Pharmco-AAper Lot #KOA01C)
11. Ginger extract (Amax, Lot #RCA245C63)

12. Grains of Paradise Extract (GoPE) (Amax, Production date 06/May/2015). The GoPE contained, amongst other things, 6-paradol at a concentration of about 10% wt/wt.

II. Methods

Methods are described below.

A. Blood Collection and Sample Preparation

All the experiments were conducted using healthy adult volunteers not taking aspirin or other medications that affect platelet aggregation. Whole blood was collected into 0.105 M buffered sodium citrate as the anticoagulant. Platelet-rich plasma (PRP) was prepared by centrifugation of whole blood at 135×g for 20 min. The residual blood sample was then centrifuged at 2,500×g for 15 min to obtain platelet-poor plasma (PPP). Platelet counts in the PRP were determined using a Horiba Micros 60 cell counter. For LTA experiments, platelet counts in PRP were adjusted to 250,000/μL using autologous donor PPP as the diluent.

B. Test Reagent Preparation

Arachidonic Acid (AA)

The stock vial (16 mM) of AA was diluted by adding 0.5 mL of deionized water to obtain a 1.6 mM AA solution. The AA solution was maintained on ice and was used within 6 hr of preparation.

Adenosine Diphosphate (ADP)

Stock solutions of ADP (200 μM) were prepared in saline and stored frozen at −80° C. A vial of stock ADP was thawed and further diluted in saline to obtain a 50 μM ADP solution. Fifty (50) μL of ADP solution (200 and 50 μM) were added to 450 μL of adjusted PRP to perform aggregation tests with 20 μM ADP and 5 μM ADP.

Collagen

Twenty five (25) juL of the stock solution of collagen (1 mg/ml) was added to 475 μL of collagen dilution buffer to obtain a 50 μg/ml working solution. Fifty (50) μL of collagen solution was added to 450 μL of adjusted PRP to perform aggregation tests. The final concentration of collagen used for aggregation testing was 5 μg/ml.

50% DMSO Solution

DMSO stock (100%) was diluted 1:1 in saline to obtain a 50% solution. For control aggregations, PRP or washed platelet suspensions were treated with this solution to obtain a final DMSO concentration of 0.1%.

Aspirin

A 200 mM stock solution of aspirin was prepared in DMSO and aliquots were stored frozen at −80° C. The stock solution was further diluted to obtain 20 mM, 2 mM and 0.2 mM aspirin solutions as shown in Table 1.

TABLE 1

| Initial Aspirin Conc. | 200 mM | 200 mM | 20 mM | 2 mM |
|---|---|---|---|---|
| Aspirin Stock Solution (μL) | 50 | 20 | 20 | 20 |
| DMSO (μL) | — | 180 | 180 | 180 |
| Final Aspirin Conc. | 200 mM | 20 mM | 2 mM | 0.2 mM |

The above prepared aspirin solutions were further diluted 1:1 in saline to obtain 100 mM, 10 mM, 1 mM, and 0.1 mM aspirin working solutions.

6-Paradol

A 200 mM stock solution of 6-paradol was prepared in DMSO and aliquots were stored frozen at −80° C. The stock solution was further diluted to obtain 20 mM, 2 mM and 0.2 mM 6-paradol solutions as shown in Table 2.

TABLE 2

| Initial 6-paradol Conc. | 200 mM | 200 mM | 20 mM | 2 mM |
|---|---|---|---|---|
| 6-paradol Stock Solution (μL) | 50 | 20 | 20 | 20 |
| DMSO (μL) | — | 180 | 180 | 180 |
| Final 6-paradol Conc. | 200 mM | 20 mM | 2 mM | 0.2 mM |

The above prepared 6-paradol solutions were further diluted 1:1 in saline to obtain 100 mM, 10 mM, 1 mM, and 0.1 mM 6-paradol working solutions.

Grains of Paradise Extract (GoPE)

GoPE was provided as a 200 mg/mL solution and from this, a stock solution (139 mg/mL, equivalent to ~200 mM of 6-paradol) was prepared in Ethanol (EtOH) and aliquots stored at −80° C. For the experiments, a fresh aliquot of stock GoPE was thawed and working solutions were prepared as shown in Table 3.

TABLE 3

| Initial GoPE Conc. | 139 mg/mL |
|---|---|
| GoPE | 20 μL |
| Ethanol | 180 μL |
| Final GoPE Conc. | 13.9 mg/mL |

Ginger Extract (GE)

GE was provided as a powder and 10 g of the powder was dissolved into 40 mL of 200 proof ethanol at 50° C. to obtain a 250 mg/mL solution. The solution was filtered through a 0.2 μm filter and aliquots of the filtrate were stored at 4° C. The 250 mg/mL GE solution was further diluted in EtOH to obtain 125 mg/mL, 62.5 mg/mL, and 31.25 mg/mL GE solutions as shown in Table 4.

TABLE 4

| Initial GE Conc. | 250 mg/mL | 125 mg/mL | 62.5 mg/mL |
|---|---|---|---|
| GE 150 mg/mL Solution | 5 mL | 5 mL | 5 mL |
| Ethanol | 5 mL | 5 mL | 5 mL |
| Final GE Conc. | 125 mg/mL | 62.5 mg/mL | 31.25 mg/mL |

GE Spiked with 6-Paradol

Twenty (20) μL of GE solution (62.5 mg/mL) was spiked with the indicated concentration of 6-paradol shown in Table 5 to obtain 6-paradol spiked GE solutions.

TABLE 5

| 6-paradol (conc.) | 6-paradol (volume) | GE (Final conc.) | 6-paradol (Final conc.) |
|---|---|---|---|
| 4 mM | 20 μL | 31.25 mg/mL | 2 mM |
| 0.4 mM | 20 μL | 31.25 mg/mL | 0.2 mM |

C. Treatment of PRP with Aspirin and 6-Paradol

The working solutions of aspirin and 6-paradol (Reagent) were added to adjusted PRP samples as shown in Table 6. The samples were incubated in a water bath at 37° C. for 30 min before performing the LTA experiments.

TABLE 6

| PRP (μL) | 1980 | 1980 | 1980 | 1980 | 1980 |
|---|---|---|---|---|---|
| Reagent Conc. (mM) | 100 | 10 | 1 | 0.1 | 50% DMSO |
| Reagent Volume (μL) | 20 | 20 | 20 | 20 | 20 |
| Final Reagent Conc. | 1 mM | 100 μM | 10 μM | 0.1 μM | 0.5% |

D. Treatment of PRP with Grains of Paradise Extract (GoPE)

The adjusted PRP was incubated with indicated concentration of GoPE (Table 7) for 30 min at 37° C.

TABLE 7

| PRP (µL) | 1990 | 1990 |
|---|---|---|
| Reagent | GoPE | GoPE |
| Reagent Conc. | 139 mg/mL | 13.9 mg/mL |
| Reagent Volume (µL) | 10 | 10 |
| Final Reagent Conc. | 0.7 mg/mL | 0.07 mg/mL |

E. Treatment of PRP with Ginger Extract

The adjusted PRP samples were treated with the GE as shown in Table 8.

TABLE 8

| PRP (µL) | 1990 |
|---|---|
| Reagent | GE |
| Reagent Conc. | 31.25 mg/mL |
| Reagent Vol (µL) | 10 |
| Final Reagent Conc. | 0.16 mg/mL |

F. Treatment of PRP with Ginger Extract Spiked with 6-Paradol

The adjusted PRP samples were treated with the GE spiked with 6-paradol as shown in Table 9.

TABLE 9

| PRP (µL) | 1990 | 1990 |
|---|---|---|
| Reagent | GE | GE |
| GE Conc. | 31.25 mg/mL | 31.25 mg/mL |
| 6-paradol Conc. | 2 mM | 0.2 mM |
| Reagent Vol (µL) | 10 | 10 |
| Final GE Conc. | 0.16 mg/mL | 0.16 mg/mL |
| Final 6-paradol Conc. | 10 µM | 1 µM |

G. Light Transmission Aggregometry (LTA)

After incubation of PRP with test articles, 450 µL of PRP were transferred into aggregation cuvettes for LTA testing. All aggregation experiments were performed on a LTA-Chronolog 700 aggregometer with Aggrolink 8 software. The instrument was set for an optical mode of data acquisition and the stir bar speed was set to 1.200 rpm. Autologous PPP was used in the reference channel of the aggregometer and baselines were set prior to addition of agonists. Fifty (50) µL of working agonist solutions (AA, ADP, and Collagen) were added to the cuvettes and tracings recorded for a minimum of 6 minutes. The maximal aggregation (MA) response was calculated using Aggrolink software for reporting the data.

Tables 10-13 summarize the results for platelet aggregation response to agonists AA (1.6 mM), ADP (20 µM, 5 µM), and collagen (5 µg/ml) in PRP treated with varying concentrations of aspirin. The abbreviation "SD" refers to standard deviation.

TABLE 10

Maximal Percent Aggregation Response to 1.6 mM Arachidonic Acid

| No. | DMSO | Aspirin (1 µM) | Aspirin (10 µM) | Aspirin (100 µM) | Aspirin (1000 µM) |
|---|---|---|---|---|---|
| 1 | 92 | 100 | 1 | 0 | QNS |
| 2 | 79 | 73 | 0 | 0 | 0 |
| 3 | 83 | 95 | 7 | 5 | 8 |
| 4 | 87 | 75 | 0 | 0 | 0 |

TABLE 10-continued

Maximal Percent Aggregation Response to 1.6 mM Arachidonic Acid

| No. | DMSO | Aspirin (1 µM) | Aspirin (10 µM) | Aspirin (100 µM) | Aspirin (1000 µM) |
|---|---|---|---|---|---|
| 5 | 80 | 0 | 0 | 0 | 0 |
| Mean | 84 | 69 | 2 | 1 | 2 |
| SD | 5 | 40 | 3 | 2 | 4 |

QNS: Quantity Not Sufficient

TABLE 11

Maximal Percent Aggregation Response to 20 µM Adenosine Diphosphate

| No. | DMSO | Aspirin (1 µM) | Aspirin (10 µM) | Aspirin (100 µM) | Aspirin (1000 µM) |
|---|---|---|---|---|---|
| 1 | 100 | 100 | 92 | 95 | 80 |
| 2 | 83 | 81 | 68 | 97 | 78 |
| 3 | 81 | 90 | 84 | 87 | 88 |
| 4 | 69 | 91 | 78 | 63 | 72 |
| 5 | 87 | 87 | 78 | 87 | 84 |
| Mean | 84 | 90 | 80 | 86 | 80 |
| SD | 11 | 7 | 9 | 14 | 6 |

TABLE 12

Maximal Percent Aggregation Response to 5 µM Adenosine Diphosphate

| No. | DMSO | Aspirin (1 µM) | Aspirin (10 µM) | Aspirin (100 µM) | Aspirin (1000 µM) |
|---|---|---|---|---|---|
| 1 | 80 | 83 | 63 | 94 | 90 |
| 2 | 67 | 92 | 84 | 75 | 86 |
| 3 | 52 | 73 | 52 | 53 | 50 |
| 4 | 75 | 78 | 82 | 63 | 71 |
| Mean | 69 | 82 | 70 | 71 | 74 |
| SD | 12 | 8 | 15 | 18 | 18 |

TABLE 13

Maximal Percent Aggregation Response to 5 µg/mL Collagen

| No. | DMSO | Aspirin (1 µM) | Aspirin (10 µM) | Aspirin (100 µM) | Aspirin (1000 µM) |
|---|---|---|---|---|---|
| 1 | 100 | 100 | 100 | 92 | 75 |
| 2 | 77 | 82 | 80 | 61 | 52 |
| 3 | 83 | 92 | 100 | 90 | 83 |
| 4 | 96 | 97 | 87 | 28 | 32 |
| 5 | 89 | 100 | 86 | 52 | 39 |
| Mean | 89 | 94 | 91 | 65 | 56 |
| SD | 9 | 8 | 9 | 27 | 22 |

Tables 14-17 summarize the results for platelet aggregation response to agonists AA (1.6 mM), ADP (20 µM and 5 µM), and Collagen (2 µg/ml) in PRP treated with varying concentrations of 6-paradol. The abbreviation "SD" refers to standard deviation.

TABLE 14

Maximal Percent Aggregation Response to 1.6 mM Arachidonic Acid

| No. | DMSO | 6-paradol (1 μM) | 6-paradol (10 μM) | 6-paradol (100 μM) | 6-paradol (1000 μM) |
|---|---|---|---|---|---|
| 1 | 92 | 96 | 99 | 0 | 0 |
| 2 | 79 | 65 | 71 | 0 | 0 |
| 3 | 83 | 98 | 87 | 9 | 3 |
| 4 | 87 | 72 | 0 | 0 | 0 |
| 5 | 80 | 77 | 0 | 0 | 0 |
| Mean | 84 | 82 | 51 | 2 | 1 |
| SD | 5 | 15 | 48 | 4 | 1 |

TABLE 15

Maximal Percent Aggregation Response to 20 μM Adenosine Diphosphate

| No. | DMSO | 6-paradol (1 μM) | 6-paradol (10 μM) | 6-paradol (100 μM) | 6-paradol (1000 μM) |
|---|---|---|---|---|---|
| 1 | 100 | 88 | 100 | 95 | 78 |
| 2 | 83 | 74 | 84 | 76 | 67 |
| 3 | 81 | 99 | 85 | 90 | 67 |
| 4 | 69 | 70 | 81 | 63 | 53 |
| 5 | 87 | 85 | 82 | 73 | 67 |
| Mean | 84 | 83 | 86 | 79 | 66 |
| SD | 11 | 12 | 8 | 13 | 9 |

TABLE 16

Maximal Percent Aggregation Response to 5 μM Adenosine Diphosphate

| No. | DMSO | 6-paradol (1 μM) | 6-paradol (10 μM) | 6-paradol (100 μM) | 6-paradol (1000 μM) |
|---|---|---|---|---|---|
| 1 | 80 | 81 | 78 | 67 | 53 |
| 2 | 67 | 92 | 96 | 81 | 59 |
| 3 | 52 | 50 | 46 | 45 | 33 |
| 4 | 75 | 83 | 77 | 57 | 55 |
| Mean | 69 | 77 | 74 | 63 | 50 |
| SD | 12 | 18 | 21 | 15 | 12 |

TABLE 17

Maximal Percent Aggregation Response to 5 μg/ml Collagen

| No. | DMSO | 6-paradol (1 μM) | 6-paradol (10 μM) | 6-paradol (100 μM) | 6-paradol (1000 μM) |
|---|---|---|---|---|---|
| 1 | 100 | 100 | 100 | 100 | 60 |
| 2 | 77 | 77 | 100 | 88 | 36 |
| 3 | 83 | 97 | 97 | 89 | 74 |
| 4 | 96 | 90 | 98 | 64 | 10 |
| 5 | 89 | 81 | 82 | 82 | 23 |
| Mean | 89 | 89 | 95 | 85 | 41 |
| SD | 9 | 10 | 8 | 13 | 26 |

Tables 18-21 summarize the results for platelet aggregation response to agonists AA (1.6 mM), ADP (20 μM and 5 μM), or Collagen (2 μg/ml) in PRP treated with Grains of Paradise Extract (GoPE), Ginger Extract (GE), or GE spiked with 6-paradol. The abbreviation "SD" refers to standard deviation.

TABLE 18

Maximal Percent Aggregation Response to 1.6 mM Arachidonic Acid

| No. | EtOH | GoPE (0.07 mg/mL) | GoPE (0.7 mg/mL) | GE 0.16 mg/mL | GE + 6-paradol (1 μM) | GE + 6-paradol (10 μM) |
|---|---|---|---|---|---|---|
| 1 | 84 | 0 | 0 | 82 | 0 | 0 |
| 2 | 60 | 0 | 0 | 0 | 0 | 0 |
| 3 | 2 | 0 | 0 | 0 | QNS | QNS |
| 4 | 75 | 0 | 0 | 75 | 0 | 0 |
| 5 | 100 | 0 | 0 | 0 | 0 | 0 |
| Mean | 64 | 0 | 0 | 31 | 0 | 0 |
| SD | 38 | 0 | 0 | 43 | 0 | 0 |

QNS: Quantity Not Sufficient

TABLE 19

Maximal Percent Aggregation Response to 20 μM Adenosine Diphosphate

| No. | EtOH | GoPE (0.07 mg/mL) | GoPE (0.7 mg/mL) | GE 0.16 mg/mL | GE + 6-paradol (1 μM) | GE + 6-paradol (10 μM) |
|---|---|---|---|---|---|---|
| 1 | 87 | 73 | 51 | 87 | 100 | 69 |
| 2 | 51 | 64 | 27 | 67 | 71 | 69 |
| 3 | 95 | 80 | 46 | 91 | QNS | QNS |
| 4 | 75 | 70 | 36 | 76 | 83 | 77 |
| 5 | 94 | 78 | 46 | 94 | 92 | QNS |
| Mean | 80 | 73 | 41 | 83 | 87 | 72 |
| SD | 18 | 6 | 10 | 11 | 13 | 5 |

QNS: Quantity Not Sufficient

TABLE 20

Maximal Percent Aggregation Response to 5 μM Adenosine Diphosphate

| No. | EtOH | GoPE (0.07 mg/mL) | GoPE (0.7 mg/mL) | GE 0.16 mg/mL | GE + 6-paradol (1 μM) | GE + 6-paradol (10 μM) |
|---|---|---|---|---|---|---|
| 1 | 91 | 71 | 36 | 72 | 74 | 63 |
| 2 | 42 | 45 | 15 | 49 | 55 | 53 |
| 3 | 93 | 67 | 31 | 100 | QNS | QNS |
| 4 | 65 | 57 | 23 | 59 | 67 | 82 |
| 5 | 100 | 82 | 25 | 100 | 89 | QNS |
| Mean | 78 | 61 | 27 | 74 | 65 | 58 |
| SD | 24 | 14 | 11 | 26 | 13 | 7 |

QNS: Quantity Not Sufficient

TABLE 21

Maximal Percent Aggregation Response to 5 μg/ml Collagen

| No. | EtOH | GoPE (0.07 mg/mL) | GoPE (0.7 mg/mL) | GE 0.16 mg/mL | GE + 6-paradol (1 μM) | GE + 6-paradol (10 μM) |
|---|---|---|---|---|---|---|
| 1 | 84 | 73 | 7 | 95 | 100 | 95 |
| 2 | 80 | 58 | 3 | 82 | 86 | 83 |
| 3 | 97 | 78 | 12 | 100 | QNS | QNS |
| 4 | 71 | 72 | 18 | 79 | 81 | 81 |
| 5 | 81 | 75 | 12 | 82 | 88 | QNS |
| Mean | 83 | 71 | 10 | 88 | 89 | 86 |
| SD | 9 | 8 | 6 | 9 | 8 | 8 |

QNS: Quantity Not Sufficient

III. Exemplary Conclusions

Exemplary conclusions based on the above data are provided below.

Effects of Aspirin on Platelet Aggregation:

Aspirin at a concentration of 1 µM did not significantly inhibit AA-mediated platelet aggregation. However, near complete inhibition of AA-mediated platelet aggregation was observed at aspirin concentrations of 10 µM aspirin and higher. Aspirin did not significantly inhibit platelet aggregation in the presence of 5 or 20 µM ADP at any of the aspirin concentrations tested. Aspirin at a concentration of 100 µM and 1000 µM inhibited collagen-mediated platelet aggregation response by about 27% and 37%, respectively, relative to that observed in control experiments using just DMSO. The 27% and 37% values were calculated by subtracting the mean platelet aggregation response observed using aspirin at the indicated concentration from the mean platelet aggregation response observed using the DMSO standard, and then the difference was divided by the mean platelet aggregation response observed using the DMSO standard.

Effects of 6-Paradol on Platelet Aggregation:

6-Paradol at a concentration of 1 µM did not significantly inhibit AA-mediated platelet aggregation response. Near complete inhibition of AA-mediated platelet aggregation was observed at a 6-paradol concentration of 10 µM or higher in most experiments. 6-Paradol did not significantly inhibit platelet aggregation response to 5 or 20 µM ADP at any concentration of 6-paradol tested. 6-Paradol did not significantly inhibit collagen-mediated platelet aggregation at 6-paradol concentrations of 100 µM or less. However, 6-paradol at a concentration of 1000 µM substantially inhibited collagen-mediated platelet aggregation response.

Effects of Grains of Paradise Extract (GoPE) on Platelet Aggregation:

GoPE at both of the tested concentrations (0.07 mg/mL and 0.7 mg/mL) completely inhibited AA-mediated platelet aggregation. GoPE at 0.07 mg/mL and 0.7 mg/mL concentrations inhibited 5 µM ADP-mediated platelet aggregation response by about 22% and 65%, respectively, relative to the control experiments using just EtOH. GoPE at 0.07 mg/mL and 0.7 mg/mL concentrations inhibited 20 µM ADP-mediated platelet aggregation response by about 10% and 50%, respectively, relative to the control experiments using just EtOH. GoPE inhibited collagen-mediated platelet aggregation response by about 14% at 0.07 mg/mL and about 88%/o at 0.7 mg/mL concentration, each relative to the control experiments using just EtOH.

Effects of Ginger Extract (GE) and Spiked Ginger Extract on Platelet Aggregation:

GE at a concentration of 0.16 mg/mL completely inhibited AA-mediated platelet aggregation in ⅗ (60%) subjects tested. When GE was spiked with 1 µM 6-paradol or greater amounts of 6-paradol, AA-mediated platelet aggregation was completely inhibited in all subjects tested. GE alone or when spiking with 6-paradol did not significantly inhibit platelet aggregation response to 20 µM ADP or collagen. At an ADP concentration of 5 µM, platelet aggregation response was inhibited by about 17% and 26% when GE was spiked with 6-paradol to produce a 6-paradol concentration of 1 or 10 µM, respectively, relative to the control experiments using just EtOH.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended embodiments rather than by the foregoing description, and all changes that come within the meaning and range of equivalency of the embodiments are intended to be embraced therein.

What is claimed is:

1. A method of treating cardiovascular disease in a patient, comprising orally administering to a patient in need thereof an effective amount of a therapeutic composition comprising ground seed of *Aframomum melegueta* or an extract thereof, to treat the cardiovascular disease, wherein there is a reduction in the incidence of platelet aggregation caused by arachidonic acid, there is a reduction in the incidence of platelet aggregation caused by adenosine diphosphate, and there is a reduction in the incidence of platelet aggregation caused by collagen.

2. The method of claim 1, wherein the ground seed of *Aframomum melegueta* or an extract thereof is the only active ingredient for treating cardiovascular disease in the therapeutic composition.

3. The method of claim 1, wherein the therapeutic composition consists of (i) ground seed of *Aframomum melegueta*, an extract thereof, or both, and (b) optionally a pharmaceutically acceptable carrier.

4. A method of reducing the risk of cardiovascular disease attributed to platelet aggregation in a patient, comprising orally administering to a patient in need thereof an effective amount of a therapeutic composition comprising ground seed of *Aframomum melegueta* or an extract thereof, to reduce the risk of cardiovascular disease attributed to platelet aggregation, wherein the cardiovascular disease attributed to platelet aggregation is acute coronary syndrome, myocardial infarction, stroke, peripheral arterial disease, transient ischemic attack, or angina, in each instance attributed to platelet aggregation, and there is a reduction in the incidence of platelet aggregation caused by arachidonic acid, there is a reduction in the incidence of platelet aggregation caused by adenosine diphosphate, and there is a reduction in the incidence of platelet aggregation caused by collagen.

5. The method of claim 4, wherein the ground seed of *Aframomum melegueta* or an extract thereof is the only active ingredient for reducing the risk of cardiovascular disease in the therapeutic composition.

6. The method of claim 4, wherein the therapeutic composition consists of (i) ground seed of *Aframomum melegueta*, an extract thereof, or both, and (b) optionally a pharmaceutically acceptable carrier.

7. The method of claim 4, wherein the risk of cardiovascular disease attributed to platelet aggregation is reduced for a duration of at least 1 week, 1 month, 3 months, or 6 months.

8. The method of claim 4, wherein the method achieves a reduction in the incidence of cardiovascular disease attributed to platelet aggregation by at least 20%, 30%, 40%, 50%, 60%, 70%, 80%, or 90% in a population of patients that receive the therapeutic composition relative to a medically analogous population of patients that do not receive the therapeutic composition.

9. The method of claim 1, wherein the cardiovascular disease is acute coronary syndrome, myocardial infarction, stroke, peripheral arterial disease, transient ischemic attack, angina, or atherosclerosis.

10. The method of claim 1, wherein the therapeutic composition is administered orally at a daily dosage in the range of from about 0.1 g to about 3 g per day.

11. The method of claim 1, wherein the therapeutic composition is administered orally at a daily dosage in the range of from about 2 g to about 3 g per day.

12. The method of claim 3, wherein the therapeutic composition is administered orally at a daily dosage in the range of from about 0.1 g to about 3 g per day.

13. The method of claim 1, wherein the administering produces less gastric bleeding than aspirin administered orally at a dosage sufficient to achieve the reduction of platelet aggregation achieved using said therapeutic composition.

14. The method of claim 1, wherein the cardiovascular disease is acute coronary syndrome or myocardial infarction.

15. The method of claim 1, wherein the cardiovascular disease is stroke.

16. The method of claim 1, wherein the cardiovascular disease is peripheral arterial disease, transient ischemic attack, or angina.

17. The method of claim 3, wherein the cardiovascular disease is acute coronary syndrome or myocardial infarction.

18. The method of claim 3, wherein the cardiovascular disease is stroke.

19. The method of claim 3, wherein the cardiovascular disease is peripheral arterial disease, transient ischemic attack, or angina.

20. The method of claim 4, wherein the cardiovascular disease attributed to platelet aggregation is acute coronary syndrome or myocardial infarction, in each instance attributed to platelet aggregation.

21. The method of claim 4, wherein the cardiovascular disease attributed to platelet aggregation is stroke attributed to platelet aggregation.

22. The method of claim 4, wherein the cardiovascular disease attributed to platelet aggregation is peripheral arterial disease, transient ischemic attack, or angina, in each instance attributed to platelet aggregation.

* * * * *